(12) United States Patent
Moloney et al.

(10) Patent No.: US 7,091,401 B2
(45) Date of Patent: Aug. 15, 2006

(54) EXPRESSION OF EPIDERMAL GROWTH FACTOR IN PLANT SEEDS

(75) Inventors: Maurice M. Moloney, Calgary (CA); Gijs Van Rooijen, Calgary (CA)

(73) Assignee: Sembiosys Genetics Inc., Calgary (CA)

( * ) Notice: Subject to any disclaimer, the term of this patent is extended or adjusted under 35 U.S.C. 154(b) by 517 days.

(21) Appl. No.: 10/324,131

(22) Filed: Dec. 20, 2002

(65) Prior Publication Data

US 2003/0177537 A1 Sep. 18, 2003

Related U.S. Application Data

(63) Continuation-in-part of application No. 09/893,525, filed on Jun. 29, 2001, now Pat. No. 6,753,167, which is a continuation-in-part of application No. 08/846,021, filed on Apr. 25, 1997, now Pat. No. 5,948,682, which is a continuation-in-part of application No. 08/366,783, filed on Dec. 30, 1994, now Pat. No. 5,650,554, which is a continuation-in-part of application No. 08/142,418, filed on Nov. 16, 1993, now abandoned, which is a continuation-in-part of application No. 07/659,835, filed on Feb. 22, 1991, now abandoned.

(51) Int. Cl.
*C12N 15/82* (2006.01)
*C12N 15/18* (2006.01)
*C12N 15/62* (2006.01)
*A01H 5/00* (2006.01)
*A01H 5/10* (2006.01)

(52) U.S. Cl. ............... 800/288; 800/278; 800/306; 800/320.1; 435/69.4; 435/69.5; 435/69.7; 435/69.8; 536/23.4; 536/23.5; 536/23.51

(58) Field of Classification Search .......... 800/278, 800/288, 306, 320.1, 322; 435/69.4, 69.5, 435/69.7, 69.8; 536/23.4, 23.5, 23.51
See application file for complete search history.

(56) References Cited

U.S. PATENT DOCUMENTS 5,162,601 A 11/1992 Slightom
2003/0074700 A1* 4/2003 Huang et al. ............... 800/288

FOREIGN PATENT DOCUMENTS

| EP | 0 348 348 A2 | 12/1989 |
|---|---|---|
| EP | 0 449 375 A2 | 10/1991 |
| EP | 0 449 376 A2 | 10/1991 |
| EP | 0 193 259 B1 | 12/1991 |
| WO | WO 93/20216 | 10/1993 |
| WO | WO 93/21320 | 10/1993 |
| WO | WO 98/21348 | 5/1998 |

OTHER PUBLICATIONS

Yoon et al. Life Sciences 64(16): 1435-1445 (1999).*
EMBL Nucleic Acid Sequence Database, *A. thaliana* gene for oleosin, Accession No. X62353, Feb. 20, 1992 Release 31.
An G., et al., New cloning vehicles for transformation of higher plants. The EMBO Journal 4(2):, 1985, 277-284.
Antoni, G. et al. A short synthetic peptide fragment of human interleukin 1 with immunostimulatory but not inflammatory activity. The Journal of Immunology 137 (10):, 1986, 3201-3204.
Batchelder, C. et al. Molecular genetics of oil body membrane proteins in *Brassica napus* and *Arabidopsis*[P8.58]. Journal of Experimental Biology, supplement 42(238): 47:, 1991.
Bevan, M., Binary *Agrobacterium* vectors for plant transformation. Nucleic Acids Research 12(22):, 1984, 8711-8721.
Bowman Vance, V. et al., Expression of lipid body protein gene during maize seed development. The Journal of Biological Chemistry 263(3):, 1988, 1476-1481.
Bowman Vance, V. et al., The major protein from lipid bodies in maize: Characterization and structure based on cDNA cloning. The Journal of Biological Chemistry 262(23):, 1987, 11275-11279.
Chen, J.C.F. et al., Cloning and secondary structure analysis of cateosin, a unique calcium-binding protein in oil bodies of plant seeds. Plant Cell Physiology 40(10):, 1999, 1079-1086.
Du S., et al. Expression of a synthetic porcine epidermal growth factor gene in plants. Second International Molecular Farming Conference, London, Ontario, Canada (1999).
Fraley R.T., et al., Expression of bacterial genes in plant cells. Proceedings of the National Academy of Science, U.S.A. 80:, 1983, 4803-4807.

(Continued)

*Primary Examiner*—David T. Fox
(74) *Attorney, Agent, or Firm*—Micheline Gravelle Bereskin & Parr

(57) ABSTRACT

The present invention provides a method of preparing epidermal growth factors in plants and transgenic plant seeds containing epidermal growth factors. The method provides an economical way to produce epidermal growth factors.

28 Claims, 6 Drawing Sheets

OTHER PUBLICATIONS

Fujikawa K., et al. Bovine Factor X1 (Stuart Factor). Mechanism of Activation by protein from Russell's Viper Venom. Biochemistry 11(26):, 1972, 4892-4898.

Goddijn, O.J.M., Plants as bioreactors. Trends in Biotechnology 13(9):, 1990, 379-387.

Hatzopoulos, P., Interaction of nuclear factors with upstream sequences of a lipid body membrane protein gene from carrot. The Plant Cell 2, 1990, 457-467.

Higo K. et al., Expression of a chemically synthesized gene for human epidermal growth factor under the control of cauliflower mosaic virus 35S promoter in transgenic tobacco. Biosci. Biotech. Biochem. 57:, 1993, 1477-1481.

Holbrook L.A. et al., Oilbody proteins in microspore-derived embryos of Brassica napus. Plant Physiology 97:, 1991, 1051-1058.

Hood A.A. et al., The hypervirulence of Agrobacterium tumefaciens A281 is encoded in a region of pTiBo542 outside of T-DNA. Journal of Bacteriology 168(3):, 1986, 1291-1301.

Huang A.H.C.,Lipid bodies. Modern Methods of Plant Analysis 1:, 1985, 145-151.

Josefsson L.G., et al. Structure of a gene encoding the 1.7S storage protein, Napin, from Brassica napus. The Journal of Biological Chemistry 262(25):, 1987, 12196-12201.

Kalinski A., et al., Molecular cloning of a protein associated with soybean seed oil bodies that is similar to thiol proteases of the papain family. The Journal of Biological Chemistry 265(23):, 1990, 13843-13848.

Kobayaski S., et al., Transformation of kiwifruit (Actinidia chinesis) and trifoliate orange (Poncirus trifoliate) with a synthetic gene encoding the human epidermal growth factor (hEGF). J. Japan Soc. Hort. Sci. 64(4):, 1996, 763-769.

Lee, K. et al., Genomic nucleotide sequence of a Brassica napus 20-kilodalton oleosin gene. Plant Physiology 96:, 1991 1395-1397.

Lee. W.S., et al., Maize oleosin is correctly targeted to seed oil bodies in Brassica napus transformed with the maize oleosin gene. Proceedings of the National Academy of Science, U.S.A. 88:, 1991, 6181-6185.

Misra S., et al., Heavy metal tolerant transgenic Brassica napus L. and Nicotina tabacum L. plants. Theoretical and Applied Genetics 78:, 1989, 161-168.

Murphy D.J., et al., Synthesis of the major oil-body membrane protein in developing rapeseed (Brassica napus) embryos. Biochemistry Journal 258:, 1991, 285-293.

Murphy, D.J., A class of amphipathic proteins associated with lipid storage bodies in plants: Possible similarities with animal serum apolipoproteins. Biochimica et Biophysica Acta 1088:, 1991, 86-94.

Murphy, D.J., et al., A class of amphipathic proteins associated with lipid storage bodies in plants: Possible similarities with animal serum apolipoproteins. Biological Abstracts 91(8):, 1991, abstract No. 84634.

Naestaed, H. et al., Caleosins: $Ca^{2+}$-binding proteins associated with lipid bodies. Plant Molecular Biology 44:, 2000, 463-476.

Nagai K., et al., Oxygen binding properties of human mutant hemoglobins sythesized in Escherichia coli. Proceedings of the National Academy of Science, U.S.A. 82:, 1985, 7252-7255.

Nuccio, M.L., et al., ATS1 and ATS3: two novel embryo-specific genes in Arabidopsis thaliana. Plant Molecular Biology 39:, 1999, 1153-1163.

Parmeneter, D.L., et al., Production of biologically active hirudin in plant seeds using oleosin partitioning. Plant Molecular Biology 29:, 1995, 1167-1180.

Qu, R. et al., Oleosin KD 18 on the surface of oil bodies in maize: Genomic and cDNA sequences and the deduced protein structure. The Journal of Biological Chemistry 265(4):, 1990, 2238-2243.

Qu, R. et al., Characteristics and biosynthesis of membrane proteins of lipid bodies in the scutella of maize (Zea mays L.). Biochemistry Journal 235:, 1986, 57-65.

Radke S.E. et al., Transformation of Brassica napus L. using Agrobacterium tumefaciens: developmentally regulated expression of reintroduced napin gene. Theoretical and Applied Genetics 75:, 1988, 685-694.

Salmanian, A-H., et al. Synthesis and expression of the gene for human epidermal growth factor in transgenic potato plants. Biotechnology Letters 18:, 1996, 1095-1098.

Scholtissek S. et al., A plasmid vector system for the expression of a triprotein consisting of galactosidase, a collagenase recognition site and a foreign gene product. Gene 62:, 1988, 55-64.

Scofield S.R., et al., Nucleotide sequence of a member of the Napin storage protein family from Brassica napus. The Journal of Biological Chemistry 262(25):, 1987, 12202-12208.

Sengupta-Gopalan C., et al. Developmentally regulated expression of the bean -phaseolin gene in tobacco seed. Proceedings of the National Academy of Science, U.S.A. 82:, 1985, 3320-3324.

Sijmons P.C., et al., Production of correctly processed human serum albumin in transgenic plants. Biotechnology 8:, 1990, 217-221.

Taylor D.C., et al., Storage-protein regulation and lipid accumulation in microspore embryos of Brassica napus L. Planta 181:, 1990, 18-26.

Van Rooijen, G.J.H. et al., Plant seed oil-bodies as carriers for foreign proteins. Bio/Technology 13:, 1995 72-77.

Van Rooijen, G.J.H., et al., Nucleotide sequence of an Arabidopsis thaliana oleosin gene. Plant Molecular Biology 18:, 1992, 1177-1179.

Vandekerckhove, J., et al., Enkephalins produced in transgenic plants using modified 2S seed storage proteins. Biotechnology 7:, 1989, 929-932.

\* cited by examiner

Phaseolin promoter | *Arabidopsis* oleosin coding sequence | Cleavage site | Optimized hEGF cDNA | Phaseolin terminator

FIGURE 2a

```
   1  attcattgtactcccagtatcattatagtgaaagttttggctctc
  46  tcgccggtggttttttacctctatttaaaggggttttccacctaa
  91  aaattctggtatcattctcacttacttgttactttaatttctca
 136  taatctttggttgaaattatcacgcttccgcacacgatatccta
 181  caaatttattatttgttaaacatttcaaaccgcataaaatttta
 226  tgaagtcccgtctatctttaatgtagtctaacattttcatattga
 271  aatataatttacttaattttagcgttggtagaaagcataaaga
 316  tttattcttattcttcttcatataaatgtttaatatacaatataa
 361  acaaattctttaccttaagaaggatttcccatttatattttaaa
 406  aatatattatcaaatattttcaaccacgtaaatctcataataa
 451  taagttgtttcaaaagtaataaaatttaactccataatttttta
 496  ttcgactgatcttaaagcaacacccagtgacacaactagccattt
 541  ttttctttgaataaaaaaatccaattatcattgtattttttttat
 586  acaatgaaaatttcaccaaacaatcatttgtggtatttctgaagc
 631  aagtcatgttatgcaaaattctataattcccatttgacactacgg
 676  aagtaactgaagatctgcttttacatgcgagacacatcttctaaa
 721  gtaattttaataatagttactatattcaagatttcatatatcaaa
 766  tactcaatattacttctaaaaaattaattagatataattaaaata
 811  ttacttttttaattttaagtttaattgttgaatttgtgactattg
 856  atttattattctactatgtttaaattgttttatagatagtttaaa
 901  gtaaatataagtaatgtagtagagtgttagagtgttaccctaaac
 946  cataaactataacatttatggtggactaattttcatatatttctt
 991  attgctttacctttcttggtatgtaagtccgtaactagaatta
1036  cagtgggttgccatgacactctgtggtcttttggttcatgcatgg
1081  gtcttgcgcaagaaaaagacaaagaacaaagaaaaaagacaaaac
1126  agagagacaaaacgcaatcacacaaccaactcaaattagtcactg
1171  gctgatcaagatcgccgcgtccatgtatgtctaaatgccatgcaa
1216  agcaacacgtgcttaacatgcactttaaatggctcacccatctca
1261  acccacacacaaacacattgccttttttcttcatcatcaccacaac
1306  cacctgtatatattcattctcttccgccacctcaatttcttcact
1351  tcaacacacgtcaacctgcatatgcgtgtcatcccatgcccaaat
1396  ctccatgcatgttccaaccaccttctctcttatataatacctata
1441  aatacctctaatatcactcacttctttcatcatccatccatccag
1486  agtactactactctactactataataccccaacccaactcatatt M  A  D  T  A  R  G  T  H  H
1531  caatactactctactATGGCGGATACAGCTAGAGGAACCCATCAC D  I  I  G  R  D  Q  Y  P  M  M  G  R  D  R
1576  GATATCATCGGCAGAGACCAGTACCCGATGATGGGCCGAGACCGA D  Q  Y  Q  M  S  G  R  G  S  D  Y  S  K  S
1621  GACCAGTACCAGATGTCCGGACGAGGATCTGACTACTCCAAGTCT R  Q  I  A  K  A  A  T  A  V  T  A  G  G  S
1666  AGGCAGATTGCTAAAGCTGCAACTGCTGTCACAGCTGGTGGTTCC L  L  V  L  S  S  L  T  L  V  G  T  V  I  A
1711  CTCCTTGTTCTCTCCAGCCTTACCCTTGTTGGAACTGTCATAGCT L  T  V  A  T  P  L  L  V  I  F  S  P  I  L
1756  TTGACTGTTGCAACACCTCTGCTCGTTATCTTCAGCCCAATCCTT
```

FIGURE 2b

```
         V  P  A  L  I  T  V  A  L  L  I  T  G  F  L
1801     GTCCCGGCTCTCATCACAGTTGCACTCCTCATCACCGGTTTTCTT

S  S  G  G  F  G  I  A  A  I  T  V  F  S  W
1846     TCCTCTGGAGGGTTTGGCATTGCCGCTATAACCGTTTTCTCTTGG

I  Y  K
1891     ATTTACAAgtaagcacacatttatcatcttacttcataattttgt
1936     gcaatatgtgcatgcatgtgttgagccagtagctttggatcaatt
1981     tttttggtagaataacaaatgtaacaataagaaattgcaaattct
2026     agggaacatttggttaactaaatacgaaatttgacctagctagct
2071     tgaatgtgtctgtgtatatcatctatataggtaaaatgcttggta Y  A  T  G  E  H  P
2116     tgatacctattgattgtgaatagGTACGCAACGGGAGAGCACCCA Q  G  S  D  K  L  D  S  A  R  M  K  L  G  S
2161     CAGGGATCAGACAAGTTGGACAGTGCAAGGATGAAGTTGGGAAGC K  A  Q  D  L  K  D  R  A  Q  Y  Y  G  Q  Q
2206     AAAGCTCAGGATCTGAAAGACAGAGCTCAGTACTACGGACAGCAA H  T  G  G  E  H  D  R  D  R  T  G  G  Q
2251     CATACTGGTGGGGAACATGACCGTGACCGTACTCGTGGTGGCCAG H  T  T  M  A  E  I  T  R  I  P  L  Y  K  G
2296     CACACTACCATGGCTGAGATCACCCGCATTCCTCTCTACAAAGGT K  S  L  R  K  A  L  K  E  H  G  L  L  E  D
2341     AAGTCTCTCCGTAAGGCGCTGAAGGAACATGGACTTCTAGAAGAC F  L  Q  K  Q  Q  Y  G  I  S  S  K  F  N  S
2386     TTCTTGCAGAAACAACAGTATGGCATCTCGAGCAAGTTCAACTCT D  S  E  C  P  L  S  H  D  G  Y  C  L  H  D
2431     GATTCAGAATGCCCTCTTTCTCATGATGGATACTGTTTGCACGAT G  V  C  M  Y  I  E  A  L  D  K  Y  A  C  N
2476     GGTGTTTGTATGTATATCGAAGCTCTTGATAAGTACGCATGCAAT C  V  V  G  Y  I  G  E  R  C  Q  Y  R  D  L
2521     TGTGTGGTTGGATACATTGGTGAGAGATGCCAATATAGGGATTTG K  W  W  E  L  R  *
2566     AAGTGGTGGGAACTTAGATAAaagcttaaataagtatgaactaaa
2611     atgcatgtaggtgtaagagctcatggagagcatggaatattgtat
2656     ccgaccatgtaacagtataataactgagctccatctcacttcttc
2701     tatgaataaacaaaggatgttatgatatattaacactctatctat
2746     gcaccttattgttctatgataaatttcctcttattattataaatc
2791     atctgaatcgtgacggcttatggaatgcttcaaatagtacaaaaa
2836     caaatgtgtactataagactttctaaacaattctaactttagcat
```

FIGURE 2c

```
2881    tgtgaacgagacataagtgttaagaagacataacaattataatgg
2926    aagaagtttgtctccatttatatattatatattacccacttatgt
2971    attatattaggatgttaaggagacataacaattataaagagagaa
3016    gtttgtatccatttatatattatatactacccatttatatattat
3061    acttatccacttatttaatgtctttataaggtttgatccatgata
3106    tttctaatattttagttgatatgtatgaaaaggtactatttga
3151    actctcttactctgtataaaggttggatcatccttaaagtgggtc
3196    tatttaattttattgcttcttacagataaaaaaaaaattatgagt
3241    tggtttgataaatattgaaggatttaaaataataataaataata
3286    aataacatataatatatgtatataaatttattataatataacatt
3331    tatctataaaaaagtaaatattgtcataaatctatacaatcgttt
3376    agccttgctggaacgaatctcaattatttaaacgagagtaaacat
3421    atttgacttttggttatttaacaaattattatttaacactatat
3466    gaattttttttttttatcagcaaagaaataaaattaaattaaga
3511    aggacaatggtgtgtcccaatccttatacaaccaacttccacaag
3556    aaagtcaagtcagagacaacaaaaaaacaagcaaggaaatttt
3601    taatttgagttgtcttgtttgctgcataatttatgcagtaaaaca
3646    ctacacataacccttttagcagtagagcaatggttgaccgtgtgc
3691    ttagcttcttttatttt́attttttttatcagcaaagaataaataaa
3736    ataaaatgagacacttcagggatgtttcaaccct tatacaaaacc
3781    ccaaaaacaagtttcctagcaccctaccaactaa
```

US 7,091,401 B2

EXPRESSION OF EPIDERMAL GROWTH FACTOR IN PLANT SEEDS

CROSS REFERENCE TO RELATED APPLICATIONS

The present application is a continuation-in-part of U.S. Ser. No. 09/893,525 filed Jun. 29, 2001, now U.S. Pat. No. 6,753,167, which is a continuation-in-part of U.S. Ser. No. 08/846,021 that was filed on Apr. 25, 1997, now U.S. Pat. No. 5,948,682, which is a continuation-in-part of U.S. Ser. No. 08/366,783 that was filed on Dec. 30, 1994, now U.S. Pat. No. 5,650,554, which is a continuation-in-part of U.S. Ser. No. 08/142,418 that was filed Nov. 16, 1993, now abandoned, which is a continuation-in-part of U.S. Ser. No. 07/659,835 that was filed on Feb. 22, 1991, now abandoned, all of which are incorporated herein by reference.

FIELD OF THE INVENTION

The present invention provides novel transgenic plant seeds comprising an epidermal growth factor as well as methods of preparing plant seeds comprising epidermal growth factors.

BACKGROUND OF THE INVENTION

Naturally occurring epidermal growth factors are polypeptides, the amino acid sequences of which for a number of vertebrate species have been reported. These include murine (Savage et al., 1972, J. Biol. Chem. 247: 7612–7621; Gray et al., 1983, Nature 303: 722–725), human (Bell et al. 1986, Nuc. Acids Res. 14: 8427–8445), rattus (Simpson et al., 1985, Eur. J. Biochem. 153: 629–637; Saggi et al., 1992, DNA and Cell Biol. 11: 481–487), porcine (Pascall et al., 1991, J. Mol. End. 6: 63–70), feline (Ohashi et al., 2002, direct submission to Genbank—accession number GI:13537341), canine (Ohashi et al., 2002, direct submission to Genbank—accession number GI:14009441), equine (PCT patent application, WO 92/16626; Stewart et al., 1994, J. Mol. End. 12: 341–350). In general, epidermal growth factors isolated from different species display a high degree of amino acid sequence identity (Carpenter and Cohen, 1979, Ann. Rev. Biochem 48:193–216; Saggi et al., 1992, DNA and Cell Biol. 11: 481–487). Analogs of epidermal growth factors are also known. (see for example, Burgess et al., 1988, Biochem 27: 4977–4985; Dudgeon et al., 1990, FEBS 261: 392–396; Saggi et al., 1992, DNA and Cell Biol. 11: 481–487; Taggart et al., 1993, Biochem. Soc. Trans. 22: 21S; U.S. Pat. No. 5,070,188). These analogs typically relate to the insertion, addition or deletion of nucleotides of the epidermal growth factor gene thereby creating a protein different from the naturally occurring epidermal growth factor.

The preparation of epidermal growth factors is well known in the art. Epidermal growth factor was initially isolated from male mouse submaxillary gland (Cohen, 1962, J. Biol. Chem 237: 1555–62.) and human urine at a concentration of 0.001 mg/L (Smith et al, 1982, Nuc. Acids. Res. 15: 4497–4482) but has also been isolated from saliva, tears, milk and blood plasma (Bennett and Schultz, 1993 Am J Surg 165:728–37; Carpenter and Cohen, 1979, Ann. Rev. Biochem 48:193–216). Epidermal growth factors can also be prepared by production in genetically engineered microorganisms, such as *Escherichia coli* containing recombinant DNA which encodes an epidermal growth factor polypeptide (e.g. Smith et al., 1982, Nucl. Acids Res. 10: 4467–4482; Oka et al., 1985, Proc Natl. Acad. Sci. 82: 7212–7216; U.S. Pat. No. 5,652,120; WO 94/25592; Tong et al. 2001, App. Micro. Biotech. 57: 674–679; EP 0 234 888 B1, U.S. Pat. No. 5,004,686, U.S. Pat. No. 4,743,679). Other microbial hosts like *Bacillus brevis* (Yamagata et al. 1989, Proc. Natl. Acad. Sci. 86: 3589–3593) and eukaryotic hosts like yeasts (see for example, Urdea et al. 1983, Proc. Natl, Acad. Sci. 80: 7461–7465; Clare et al., 1991, Gene 15: 205–212) have been used for the production of epidermal growth factor.

The low costs associated with growing plants, make plants an attractive host for the production of epidermal growth factors. To the best of the present inventors knowledge only limited success has been reported for the production of an epidermal growth factor in plants. Higo et al. 1993 (Biosci. Biotech. Biochem. 57: 1477–1481) report the expression of human epidermal growth factor in the leaves of tobacco at a level of 0.001% (approximately 60 pg/mg protein) of total soluble protein. Note that the epidermal growth factor construct was optimized for *E. coli* codon usage. An expression level of approximately 120 pg of epidermal growth factor per mg of total soluble proteins in potato tubers was achieved by Salmanian et al. 1996, Biotech. Lett. 18: 1095–1098. Kobayaski et al., 1996, J. Japan Soc. Hort. Sci. 64(4): 763–769 disclose the expression of 65 pg of epidermal growth factor per mg of soluble protein in the leaves of kiwi fruit and 113 pg of epidermal growth factor per mg of soluble protein in the trifoliate orange leaves. Hooker et al. disclose (WO 98/21348) an epidermal growth factor expression level of 4100 pg/mg of total soluble protein in transgenic calli. Finally Du et al., reported at the Second International Molecular Farming Conference, London, Ontario, Canada (1999) a porcine epidermal growth factor expression level of 0.12% of total protein in tobacco leaves. A review of the prior art reveals no successful accumulation of epidermal growth factor in seeds.

Although methods for producing epidermal growth factor are well known to skilled artisans, the existing methods are relatively expensive, especially when large production volumes are required. Accordingly there is a need in the art for additional economical production methods of epidermal growth factor.

SUMMARY OF THE INVENTION

The present inventors have discovered a cost effective method for the preparation of epidermal growth factor in the seeds of plants. The method involves expressing an epidermal growth factor in plant seeds as a fusion protein with an oil body protein so that the epidermal growth factor has biological activity.

Accordingly, the present invention provides a method for the expression of an epidermal growth factor in a plant comprising:

(a) introducing into a plant cell a chimeric nucleic acid sequence comprising:
  (1) a first nucleic acid sequence capable of regulating the transcription in said host cell of
  (2) a second nucleic acid sequence, wherein said second sequence encodes a recombinant fusion polypeptide and comprises (i) a nucleic acid sequence encoding a sufficient portion of an oil body protein to provide targeting of the recombinant fusion polypeptide to a lipid phase, linked in frame to (ii) a nucleic acid sequence encoding said epidermal growth factor; and
  (3) a third nucleic acid sequence encoding a termination region functional in said plant cell; and (b) growing said plant cell to produce said recombinant fusion polypeptide.

In another aspect the invention provides a chimeric nucleic acid sequence, capable of being expressed in association with an oil body of a plant cell, comprising:
(1) a first nucleic acid sequence capable of regulating the transcription in said plant cell
(2) a second nucleic acid sequence, wherein said second sequence encodes a recombinant fusion polypeptide and comprises (i) a nucleic acid sequence encoding a sufficient portion of an oil body protein to provide targeting of the recombinant fusion polypeptide to a lipid phase, linked in reading frame to (ii) a nucleic acid sequence encoding an epidermal growth factor; and
(3) a third nucleic acid sequence encoding a termination region functional in said host cell.

In a further aspect, the instant invention provides plant seeds comprising epidermal growth factor.

BRIEF DESCRIPTION OF THE DRAWINGS

The invention will now be described in relation to the drawings in which:

FIG. 2a–2b are the nucleic acid sequence (SEQ. ID. NO.:10) and deduced amino acid sequence (SEQ. ID. NO.: 11) of the oleosin-epidermal growth factor fusion sequence including the phaseolin promoter and terminator.

DETAILED DESCRIPTION OF THE INVENTION

Figure 1:
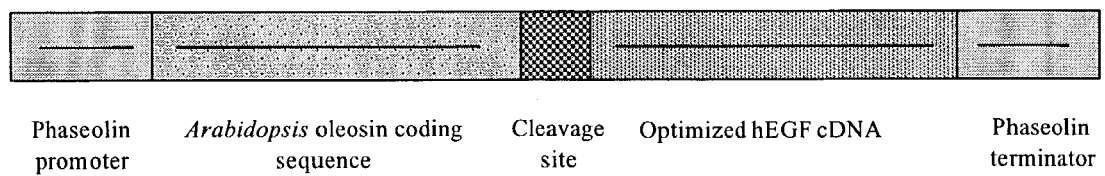
FIG. 1 is a schematic diagram of the oleosin-epidermal growth factor fusion construct.

The present invention relates to the production of epidermal growth factors. Epidermal growth factors, also referred to as urogastrone in humans, are peptide growth factors synthesized predominantly in the salivary glands and kidneys and to a lesser extent in the mammary glands, small intestine, pancreas and liver (Buret et al, 1998, Infect. and Imm. 66: 4917–4923.). In general, epidermal growth factors are mitogenic polypeptides that are active on a variety of cell types, especially but not exclusively epithelial cells. The mitogenic effects of epidermal growth factor include stimulation of transport, activation of glycolysis, activation of extracellular macromolecule synthesis, activation of RNA and protein synthesis, initiation of DNA synthesis, increased cell multiplication (Carpenter and Cohen, 1979, Ann. Rev. Biochem 48:193–216). Accordingly it has been recognized that the use of epidermal growth factors results in improvements of the production economics in industries such as the livestock industry including for example wool harvesting (Holden, 1998, Science 281: 511) and as a feed supplement to enhance pig health and production (http://www.albertapork.com/producers/cidf.htm). As hereinbefore mentioned, the present invention provides transgenic plant seeds comprising an epidermal growth factor as well as methods of preparing plant seeds comprising epidermal growth factors.

Accordingly the present invention provides a method for the expression of an epidermal growth factor in a plant cell comprising:

(a) introducing into a plant cell a chimeric nucleic acid sequence comprising:
(1) a first nucleic acid sequence capable of regulating the transcription in said plant cell of
(2) a second nucleic acid sequence, wherein said second nucleic acid sequence encodes a recombinant fusion polypeptide and comprises (i) a nucleic sequence encoding a sufficient portion of an oil body protein to provide targeting of the recombinant fusion polypeptide to a lipid phase, linked in frame to (ii) a nucleic sequence encoding an epidermal growth factor; and
(3) a third nucleic acid sequence encoding a termination region functional in said plant cell; and
(b) growing said plant cell to produce said recombinant fusion polypeptide.

The term "oil body protein" as used herein means a protein that can naturally associate with oil bodies or can be isolated using a standard oil body preparation protocol. An oil body preparation protocol is described in van Rooijen and Moloney, 1995, Bio/Technology, 13:72–77.

In one embodiment, the oil body protein is a plant oleosin and shares sequence homology with other plant oleosins such as the oleosin isolated from *Arabidopsis thaliana* (SEQ.ID.NO: 1) or *Brassica napus* (SEQ.ID.NO.: 2). In another embodiment, the oil body protein is a caleosin or calcium binding protein from plant, fungal or other sources and shares sequence homology with plant caleosins such as the caleosin isolated from *Arabidopsis thaliana* (SEQ.ID.NO.:3 and SEQ.ID.NO.: 4) In another embodiment the oil body protein is a steroleosin (SEQ.ID.NO.:5), a sterol binding dehydrogenase (Lin L-J et al, (2002) Plant Physiol 128: 1200–1211).

The term "epidermal growth factor" as used herein comprises any active epidermal growth factor, including murine, human, rattus, porcine, feline, canine, and equine or any biologically active analogs or fragments thereof, including epidermal growth factor derivatives which have been obtained by, adding, deleting or substituting amino acids or by otherwise modifying the structure of any naturally occurring epidermal growth factor.

The term "nucleic acid sequence" refers to a sequence of nucleotide or nucleoside monomers consisting of naturally occurring bases, sugars and intersugar (backbone) linkages. The term also includes modified or substituted sequence comprising non-naturally occurring monomers or portions thereof, which function similarly. The nucleic acid sequences of the present invention may be ribonucleic (RNA) or deoxyribonucleic acids (DNA) and may contain naturally occurring bases adenine, guanine, cytosine, thymidine and uracil. The sequences may also contain modified bases such as xanthine, hypoxanthine, 2-aminoadenine, 6-methyl, 2 propyl and other alkyl adenines, 5 halo uracil, 5 halo cytosine, 6-aza uracil, 6-aza cytosine, abd 6-aza thymine, pseudo uracil, 4-thiouruacil, 8-halo adenine, 8-amino adenine, 8-thiol adenine, 8-thiolalkyl adenines, 8-hydroxyl, adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-thrifluoromethyl uracil and 5-trifluoro cytosine.

The term "sufficient portion of an oil body protein to provide targeting of the recombinant fusion polypeptide to a lipid phase" means any oil body protein or any analog or portion thereof, including oleosin, caleosin or steroleosin derivatives which have been obtained by, adding, deleting or substituting amino acids or by otherwise modifying the structure of any naturally occurring oleosin, caleosin or steroleosin which is capable of targeting to a lipid phase. Lipid phase is intended to mean any subcellular structure comprising triacylglycerides, including oil bodies and other organelles comprising membranes or membrane like structures such as the endoplasmatic reticulum or the chloroplast. In a preferred embodiment the lipid phase is an oil body.

The nucleic acid and amino acid sequences of numerous epidermal growth factors including murine (Savage et al., 1972, J. Biol. Chem. 247: 7612–7621; Gray et al., 1983, Nature 303: 722–725), human (Bell et al. 1986, Nuc. Acids Res. 14: 8427–8445), rattus (Simpson et al., 1985, Eur. J. Biochem. 153: 629–637; Saggi et al., 1992, DNA and Cell Biol. 11: 481–487), porcine (Pascall et al., 1991, J. Mol. End. 6: 63–70), feline (Ohashi et al., 2002, direct submission to Genbank—accession number GI:13537341), canine (Ohashi et al., 2002, direct submission to Genbank—accession number GI:14009441), equine (PCT patent application, WO 92/16626; Stewart et al., 1994, J. Mol. End. 12: 341–350) Analogs of epidermal growth factors are also known. (see for example, Burgess et al., 1988, Biochem 27: 4977–4985; Dudgeon et al., 1990, FEBS 261: 392–396; Saggi et al., 1992, DNA and Cell Biol. 11: 481–487; Taggart et al., 1993, Biochem. Soc. Trans. 22: 21S; U.S. Pat. No. 5,070,188). Based on the sequences cDNA clones comprising the genetic material encoding the epidermal growth factors may be prepared and oil body protein fusion genes may be prepared in accordance with the present invention and practicing techniques commonly known to those skilled in the art (see e.g. Sambrook et al. (1990), Molecular Cloning, 2nd ed., Cold Spring Harbor Press).

To identify other epidermal growth factors having desired characteristics, a nucleic acid probe may be designed and prepared to identify additional epidermal growth factors. The nucleic acid probe may be used to screen cDNA or genomic libraries from any living cell or virus. Sequences which hybridize with the probe under stringent conditions may then be isolated. Given the sequence identity of the epidermal growth factors isolated from different species to date (Carpenter and Cohen, 1979, Ann. Rev. Biochem 48:193–216; Saggi et al., 1992, DNA and Cell Biol. 11: 481–487), epidermal growth factor from a broad range of species may be isolated according to this method.

Epidermal growth factor sequences may also be isolated by screening expression libraries. Antibodies against existing epidermal growth factors may be obtained and expression libraries may be screened with these antibodies essentially as described by Huynh et al. (1985, in DNA cloning, Vol 1, a Practical Approach ed. D. M. Glover, IRL Press). Expression libraries may be prepared from any living cell or virus.

Other epidermal growth factors may be discovered by those skilled in the art. The actual epidermal growth factor sequence which is selected is not of critical importance and may be as desired. It is to be clearly understood that any epidermal growth factor may be employed without departing from the spirit or scope of the present invention.

The chimeric nucleic acid sequences which encode the oil body protein-epidermal growth factor fusion proteins of the present invention can be incorporated in a known manner into a recombinant expression system which ensures expression in the plant host cell. Accordingly, the present invention also includes a recombinant expression vector comprising a chimeric nucleic acid sequence operatively linked to a regulatory sequence and termination region suitable for expression in a host cell. In one embodiment the invention provides a chimeric nucleic acid sequence, capable of being expressed in association with an oil body of a plant cell, comprising:
(1) a first nucleic acid sequence capable of regulating the transcription in said plant cell;
(2) a second nucleic acid sequence, wherein said second sequence encodes a recombinant fusion polypeptide and comprises (i) a nucleic acid sequence encoding a sufficient portion of an oil body protein to provide targeting of the recombinant fusion polypeptide to a lipid phase, linked in reading frame to (ii) a nucleic acid sequence encoding an epidermal growth factor; and
(3) a third nucleic acid sequence encoding a termination region functional in said host cell.

The nucleic acid sequence encoding the epidermal growth factor may be genetically fused upstream or downstream of the nucleic acid sequence encoding the oil body protein and concatamers containing repetitive units of the epidermal growth factor may be employed. In preferred embodiments, the epidermal growth factor gene is fused downstream of the oleosin gene.

The present invention provides plant seeds which recombinantly express epidermal growth factor. In a preferred embodiment of the present these seeds are obtained from a dicotelydenous plant. In a yet further preferred embodiment the seeds are exalbuminous seeds. In a further preferred embodiment of the instant invention the plant seeds are obtained from the group of plant species comprising: rapeseed (*Brassica* spp.), linseed/flax (*Linum usitatissimum*), safflower (*Carthamus tinctorius*), sunflower (*Helianthus annuus*), maize (*Zea mays*), soybean (*Glycine max*), mustard (*Brassica* spp. and *Sinapis alba*), crambe, (*Crambe abyssinica*), eruca (*Eruca sativa*), oil palm (*Elaeis guineeis*), cottonseed (*Gossypium* spp.), groundnut (*Arachis hypogaea*), coconut (*Cocus nucifera*), castor bean (*Ricinus communis*), coriander (*Coriandrum sativum*), squash, (*Cucurbita maxima*), Brazil nut (*Bertholletia excelsa*) and jojoba (*Simmondsia chinensis*). It is expected that the epidermal growth factor is expressed in all embryonic tissue, although difference in expression levels may be detected in different tissues of the embryonic axis and the cotyledon. In a further preferred embodiment of the instant invention the epidermal growth factor is expressed by a seed-specific promoter. Preferably the seed specific promoter is selected from the group of promoters consisting of a phaseolin, arcelin, USP, 2S storage protein, legumin-like seed storage protein, oleosin, caleosin or steroleosin promoter.

(I) Cloning, Plant Transformation and Regeneration

Cloning and Transformation Vectors

Two types of vectors are routinely employed. The first type of vector is used for the genetic-engineering and assembly of constructs and typically consists of a backbone such as found in the pUC family of vectors, enabling replication in easily-manipulated and maintained gram negative bacteria such as *E. coli*. The second type of vector typified by the Ti and Ri plasmids, specify DNA transfer functions and are used when it is desired that the constructs be introduced into the plant and stably integrated into its genome via *Agrobacterium*-mediated transformation.

A typical construct consists, in the 5' to 3' direction, of a regulatory region complete with a promoter capable of directing expression in plants (preferably seed-specific expression), a protein coding region, and a sequence containing a transcriptional termination signal functional in plants. The sequences comprising the construct may be either natural or synthetic or any combination thereof.

Both non-seed specific promoters, such as the 35-S CaMV promoter (Rothstein et al., 1987; Gene 53: 153–161) and seed-specific promoters such as the phaseolin promoter (Sengupta-Gopalan et al., 1985; PNAS USA 82: 3320–3324), *Arabidopsis* 18 kDa oleosin promoter (Van Rooijen et al., 1992; Plant Mol. Biol. 18:1177–1179), USP promoter (Baumlein et al. 1991. Mol Gen Benet 225: 459–467.), arcelin promoter (Goossens et al. 1999; Plant Physiology 120: 1095–1104) and the flax seed specific promoters in PCT patent application WO 01/16340 (i.e. oleosin, 2S storage protein promoter and legumin-like seed storage protein promoter) may be used, however seed specific promoters are preferred. In addition to the promoter, the regulatory region contains a ribosome binding site enabling translation of the transcripts in plants and may also contain one or more enhancer sequences, such as the AMV leader (Jobling and Gehrke 1987; Nature 325: 622–625), to increase the expression of product.

The coding region of the construct will typically be comprised of sequences encoding a ligand fused in frame to an oleosin, caleosin, steroleosin or other oil body protein and ending with a translational termination codon. The sequence for the oil body protein may be comprised of any DNA sequence, or part thereof, natural or synthetic, sufficient to encode a protein that can be correctly targeted to, and stably expressed on, an oil body. A detailed description of the characteristics of such a sequence has been reported previously in Moloney, 1993; PCT Patent Appl. WO 93/21320 which is hereby incorporated by reference. The sequence may also include introns. The ligand-encoding region may in turn be comprised of any individual, or combination of, ligand sequences identified as described above. If desired, a protease or chemical recognition site may be engineered between the ligand and the target protein to enable proteolytic removal of the ligand from the target protein in the course of purification.

The region containing the transcriptional termination signal may comprise any such sequence functional in plants such as the nopaline synthase termination sequence and additionally may include enhancer sequences to increase the expression of product.

The various components of the construct are ligated together using conventional methods, typically into a pUC-based vector. This construct may then be introduced into an *Agrobacterium* vector and subsequently into host plants, using one of the transformation procedures outlined below.

Transformation of Plants

A variety of techniques is available for the introduction of DNA into host cells. For example, the chimeric DNA constructs may be introduced into host cells obtained from dicotyledonous plants, such as tobacco, and oleaginous species, such as *B. napus* using standard *Agrobacterium* vectors; by a transformation protocol such as that described by Moloney et al., 1989, (Plant Cell Rep., 8: 238–242), Hinchee et al., 1988, (Bio/Technol., 6: 915–922), Ying et al., 1992, (Plant Cell Reports 11: 581–585 or Orlikowska et al., 1995, (Plant Cell, Tissue and Organ Culture 40: 85–91); or other techniques known to those skilled in the art. For example, the use of T-DNA for transformation of plant cells has received extensive study and is amply described in EPA Serial No. 120,516; Hoekema et al., 1985, (Chapter V, In: The Binary Plant Vector System Offset-drukkerij Kanters B. V., Alblasserdam); Knauf, et al., 1983, (Genetic Analysis of Host Range Expression by *Agrobacterium*, p. 245, In Molecular Genetics of the Bacteria-Plant Interaction, Puhler, A. ed., Springer-Verlag, NY); and An et al., 1985, (EMBO J., 4: 277–284). Conveniently, explants may be cultivated with *A. tumefaciens* or *A. rhizogenes* to allow for transfer of the transcription construct to the plant cells. Following transformation using *Agrobacterium* the plant cells are dispersed in an appropriate medium for selection, subsequently callus, shoots and eventually plantlets are recovered. The *Agrobacterium* host will harbour a plasmid comprising the vir genes necessary for transfer of the T-DNA to the plant cells. For injection and electroporation, (see below) disarmed Ti-plasmids (lacking the tumour genes, particularly the T-DNA region) may be introduced into the plant cell.

The use of non-*Agrobacterium* techniques permits the use of the constructs described herein to obtain transformation and expression in a wide variety of monocotyledonous and dicotyledonous plants and other organisms. These techniques are especially useful for species that are intractable in an *Agrobacterium* transformation system. Other techniques for gene transfer include biolistics (Sanford, 1988, Trends in Biotech., 6: 299–302), electroporation (Fromm et al., 1985, Proc. Natl. Acad. Sci. USA, 82: 5824–5828; Riggs and Bates, 1986, Proc. Natl. Acad. Sci. USA 83: 5602–5606) or PEG-mediated DNA uptake (Potrykus et al., 1985, Mol. Gen. Genet., 199: 169–177).

In a specific application, such as to *B. napus*, the host cells targeted to receive recombinant DNA constructs typically will be derived from cotyledonary petioles as described by Moloney et al., (1989, Plant Cell Rep., 8: 238–242). Other examples using commercial oil seeds include cotyledon transformation in soybean explants (Hinchee et al., 1988. Bio/Technology, 6: 915–922) and stem transformation of cotton (Umbeck et al., 1981, Bio/Technology, 5: 263–266).

Regeneration and Analysis of Transgenic Plants

Following transformation, the cells, for example as leaf discs, are grown in selective medium. Once shoots begin to emerge, they are excised and placed onto rooting medium. After sufficient roots have formed, the plants are transferred to soil. Putative transformed plants are then tested for presence of a marker. Southern blotting is performed on genomic DNA using an appropriate probe, for example an epidermal growth factor gene to show that integration of the desired sequences into the host cell genome has occurred.

The expression cassette will normally be joined to a marker for selection in plant cells. Conveniently, the marker may be resistance to a herbicide, e.g. phosphinothricin or glyphosate, or more particularly an antibiotic, such as kanamycin, G418, bleomycin, hygromycin, chloramphenicol, or the like, Alternatively, a positive selection system such as the Positech® selection can be utilized (Haldrup A, Petersen S G & Okkels F T, 1998. Positive selection: a plant selection principle based on xylose isomerase, an enzyme used in the food industry. *Plant Cell Reports* 18 pp 76–81). The particular marker employed will be one which will allow for selection of transformed cells compared with cells lacking the introduced recombinant DNA.

The fusion peptide in the expression cassette constructed as described above, expresses at least preferentially in developing seeds. Accordingly, transformed plants grown in accordance with conventional ways, are allowed to set seed. See, for example, McCormick et al. (1986, Plant Cell Reports, 5: 81–84). Northern blotting can be carried out using an appropriate gene probe with RNA isolated from tissue in which transcription is expected to occur, such as a seed embryo. The size of the transcripts can then be compared with the predicted size for the fusion protein transcript.

Oil body proteins are then isolated from the seed and analyses performed to determine that the fusion peptide has been expressed. Analyses can be for example by SDS-PAGE. The fusion peptide can be detected using an antibody to the oleosin portion of the fusion peptide. The size of the fusion peptide obtained can then be compared with predicted size of the fusion protein.

Two or more generations of transgenic plants may be grown and either crossed or selfed to allow identification of plants and strains with desired phenotypic characteristics including production of recombinant proteins. It may be desirable to ensure homozygosity of the plants, strains or lines producing recombinant proteins to assure continued inheritance of the recombinant trait. Methods of selecting homozygous plants are well know to those skilled in the art of plant breeding and include recurrent selfing and selection and anther and microspore culture. Homozygous plants may also be obtained by transformation of haploid cells or tissues followed by regeneration of haploid plantlets subsequently converted to diploid plants by any number of known means, e.g.: treatment with colchicine or other microtubule disrupting agents.

(II) Recovery of the Polypeptide

The present invention also includes a fusion polypeptides encoded for by a chimeric nucleic acid sequence comprising (i) a nucleic acid sequence encoding a sufficient portion of an oil body protein to provide targeting of the fusion polypeptide to an oil body linked in reading frame to (ii) a nucleic acid sequence encoding a epidermal growth factor. Preferably the fusion polypeptide displays growth hormone activity. Consequently, the present invention includes a fusion polypeptide comprising an epidermal growth factor wherein the expressed epidermal growth factor moiety is biologically active. In preferred embodiments of the invention, the fusion polypeptide comprises an oil body protein fused to a epidermal growth factor, wherein the chimeric protein displays epidermal growth factor activity.

The invention further provides methods for the separation of the fusion protein from host cell components by partitioning of the oil body fraction. Optionally, the recombinant epidermal growth factor may be released from the fusion protein via specific cleavage of the epidermal growth factor—oil body protein fusion. Optionally a cleavage site may be located prior to the N-terminus and after the C-terminus of the epidermal growth factor allowing the fusion polypeptide to be cleaved and separated by phase separation into its component peptides.

In preferred embodiments of the present invention, seeds are crushed upon harvesting by grinding, pulverizing or otherwise breaking open the seed cells using milling equipment, for example flaking rolls, disk mills, colloid mils, pin mills, orbital mills IKA mills or industrial style homogenizers. In one embodiment of the present invention, the crushed seed fraction may directly be employed as an ingredient to formulate compositions, such as animal feed compositions, comprising epidermal growth factor. In alternative embodiments of the invention a seed fraction comprising epidermal growth factor is isolated. In a preferred embodiment of the present invention, the isolated seed fraction comprises intact oil bodies. In order to isolate the oil body fraction of the seeds, plant seeds are preferably first crushed. In one embodiment the crushed seed fraction is subsequently submitted to density centrifugation resulting in a separation of the oil body fraction from the aqueous seed fraction. Density centrifugation may be accomplished using decantation centrifuges, including 2-phase and 3-phase decanters, hydrocyclones or disc stack centrifuges. It is also possible to separate the oil body fraction from the aqueous fraction employing size exclusion methods such as membrane ultrafiltration and crossflow microfiltration. The oil bodies may be washed one or more times using preferably water, buffered solutions or other aqueous solutions in order to remove undesirable seed components.

In a further preferred embodiment the epidermal growth factor polypeptide is purified from the seed cells. This is particularly advantageously done by first isolating the oil body fraction as hereinbefore described and subsequently separating the epidermal growth factor polypeptide from the oil body fraction. If a linker comprising a protease cleavage site has been included in the expression cassette, a protease specific for the recognition motif may be added to the oil body preparation. This results in the release of the epidermal growth factor from the oil body. A centrifugation step will result in partitioning of the epidermal growth factor into the aqueous phase. Subsequent purification steps known to the skilled biochemist may be applied to the aqueous fraction in order to obtain a further degree of purity if so desired.

The following non-limiting examples are illustrative of the present invention:

EXAMPLES

Example 1

In this example, the expression of epidermal growth factor in *Arabidopsis* seeds is described as well as the purification of total seed extracts and oil bodies comprising epidermal growth factor.

Optimization of hEGF Coding Sequence

The mature hEGF amino acid sequence was downloaded from NCBI (Locus AAF85970; Quanhong, Y., Y. Rihe, P. and Aisheng, X., 2000). The coding sequence was then optimized for *Arabidopsis* usage using the coding usage table from the Codon Usage Database (www.kazsa.or.jp/codon). The two most frequently used codons were alternatively chosen for each amino acid. The final optimized epidermal growth factor sequence had 41% GC content and was scanned for any trouble sequences such as: infrequent codons in dicots, AT-rich codons, poly-adenylation signals (i.e. AATAAA), RNA-destabilizing sequence ATTTA, 5'-intron splice sites (GTAAAA, GTAAGT, GTACGT), and 3'-intron splice sites (GCAG).

Construction of Oleosin-Epidermal Growth Factor Gene Fusion

The optimized hEGF gene was cloned into plasmid pSBS4010. The pSBS4010 plasmid contains the phaseolin promoter (Sengupta-Gopalan et al., 1985; PNAS USA 82: 3320–3324) and terminator sequences. These sequences flank the *Arabidopsis* oleosin sequence (van Rooijen G J et al. 1992; Plant Mol Biol 18: 1177–9.) and the 5' region of the DNA sequence encoding the chymosin cleavage site (see for example the chymosin pro-peptide cleavage site in WO 98/49326). The hEGF sequence was synthesized using bridging PCR with two main primers, CB1121 (SEQ. ID. NO.:6), homologous to the 5'-end of the hEGF sequence and included an engineered XhoI site within a small portion of the 3'-end of the DNA sequence encoding the chymosin cleavage site, and CB1120 (SEQ. ID. NO.:7), homologous to the 3'-end of the hEGF sequence plus an engineered HindIII site.

```
CB1121-  (5'-CAGTATGGCATCTCGAGCAAGTTCAACTCTGATT            SEQ.ID.NO.:6
         CAGAATGCCCTCTTTCTCATGATGGATACTGTTTGCACGATGGTGTTTGT
         ATGTATATCGAAGCTCTTGATAAG-3')-

CB1120-  (5'-TTTAAGCTTTTATCTAAGTTCCCACCACTTCAAA            SEQ.ID.NO.7
         TCCCTATATTGGCATCTCTCACCATGTATCCAACCACACAATTGCATGC
         GTACTTATCAAGAGCTTCGATATAC-3')-
```

The two main primers overlapped by 22 bases in the middle to form the entire optimized hEGF sequence. Two 21-base smaller primers (CB1122 (SEQ. ID. NO. 8) and CB1123 (SEQ. ID. NO.:9)) were designed to amplify the final product once the main primers were joined.

CB1122-(5'-CAGTATGGCATCTCGAGCAAG-3')-SEQ. ID. NO. 8

CB1123-(5'-TTTAAGCTTTTATCTAAGTTC-3')-SEQ. ID. NO. 9

To create the final EGF construct, the pSBS4010 plasmid is digested with XhoI and HindIII and the plasmid and above fragment ligated. The correct construction of the final insert was verified by sequencing.

FIG. 1 is a schematic diagram of the oleosin-epidermal growth factor fusion construct. The oleosin coding sequence, the phaseolin promoter (Sengupta-Gopalan et al., 1985; PNAS USA 82: 3320–3324) and terminator sequence, the DNA sequence encoding the chymosin cleavage site and the epidermal growth factor cDNA sequence are indicated. FIG. 2 shows the nucleic acid sequence (SEQ. ID. NO.:10) and deduced amino acid sequence (SEQ. ID. NO.:11) of the oleosin-epidermal growth factor fusion sequence along with the phaseolin promoter and terminator. The deduced amino acid sequence of the oleosin has been bolded and the epidermal growth factor has been italicized. A chymosin cleavage site has been underlined.

*Agrobacterium* and *Arabidopsis* Transformation

*Arabidopsis thaliana* cv. Columbia (C24) is used for all the experiments. Seeds are planted on the surface of a soil mixture (two-thirds Redi-earth and one-third perlite with a pH=6.7) or an *Arabidopsis* soil mixture supplied by Lehle Seeds (perlite, vermiculite, peat, terra-green, with a pH=5.5) in 4 inch pots and covered with window screen material. The pots are placed inside a dome at 4° C. for four days for a cold treatment and subsequently moved to 24° C. growth room with constant light at about 150 μE and 50% relative humidity. The plants are irrigated at 2–3 day interval and fertilized weekly with 1% of Peters 20-19-18 20-20-20. Each pot contains about 2 to 5 5-6 plants. When plants reach about 2 cm in height, the primary bolts are cut to encourage the growth of secondary and tertiary bolts. 4 to 5 days after cutting the primary bolts, the plants are ready to be infected with *Agrobacterium*. The pSBS4010EGF plasmid was transformed into electrocompetent *Agrobacterium* EHA101. The pots with *Arabidopsis* plants are inverted and infected with 500 ml of a re-suspension an overnight *Agrobacterium* culture containing the plant transformation vector of interest for 20 seconds. It is critical that the *Agrobacterium* culture contains 5% sucrose and 0.05% of the surfactant Silwet L-77 (Lehle Seeds). The pots are subsequently covered with a transparent plastic dome for 24 hours to maintain higher humidity. The plants are allowed to grow to maturity and seeds (untransformed and transformed) are harvested. For selection of transgenic lines, the putative transformed seeds are sterilized in 20% commercial bleach for 15 min and then rinsed at least four times with ddH$_2$O. About 1000 sterilized seeds are mixed with 0.6% top agar and evenly spread on a half strength MS plate (Murashige and Skoog, 1962, Physiologia Plantarum 15: 473–497) containing 3% sucrose and 80 μM of the herbicide phosphinothricin (PPT) DL. The plates are then placed in a growth room with light regime 8 hr dark and 16 hr light at 24° C. After 7 to 10 days, putative transgenic seedlings are green and growing whereas untransformed seedlings are bleached. After the establishment of roots the putative transgenic seedlings are individually transferred to pots (the individually plants are irrigated in 3 day interval and fertilized with 1% Peters 20–19–18 in 5 day interval) and allowed to grow to maturity. The pots are covered with a transparent plastic dome for three days to protect the sensitive seedlings. After 7 days the seedlings are covered with a seed collector from Lehle Seeds to prevent seed loss due to scattering. Seeds from these transgenic plants are harvested individually and ready for analysis.

Total Seed Extract Preparation

Approximately 40 *Arabidopsis* seeds (T2 seed) were ground in 50 uL buffer (50 mM Tris pH 8.0) in microfuge tube using Stir-Pak laboratory mixer. 50 uL SDS-PAGE 2× loading buffer (100 mM Tris pH 6.8, 20% glycerol, 4% SDS, 2 mg/mL bromophenol blue, 200 mM DTT) was added to sample, boiled for 5 minutes and centrifuged at maximum speed for 2 minutes.

Oil Body Extract Preparation

Seeds are ground in mortar and pestle in 5 volumes of oil body extraction (OBE) buffer (0.4 M sucrose, 0.5 M NaCl, 50 mM Tris pH 8.0) and a pinch of acid washed sand. The extract is spun in microfuge at maximum speed for 10 min. Oil bodies are removed to a new microfuge tube. The debris pellet from the first microfuge tube was resuspended in approximately 500 uL OBE and respun. The oil bodies are added to first aliquot. The oil body fraction is washed in high stringency wash buffer (8 M urea, 100 mM Na$_2$CO$_3$; freshly made) and centrifuged for 10 min at maximum speed. The soluble fraction (undernatant) is removed and the oil bodies washed in dH$_2$O and centrifuged at maximum speed for 10 min. The undernatant is removed and the oil bodies resuspended in approximately 10 μL of dH$_2$O. Soluble proteins were quantified using the BCA Protein assay (Pierce) and analyzed on a 15% SDS-PAGE followed by Western blotting. An anti-EGF rabbit antiserum was used as the primary antibody; and anti-rabbit-IgG [H+L]-AP conjugate (Bio-Rad) was used as the secondary antibody.

Figure 3:
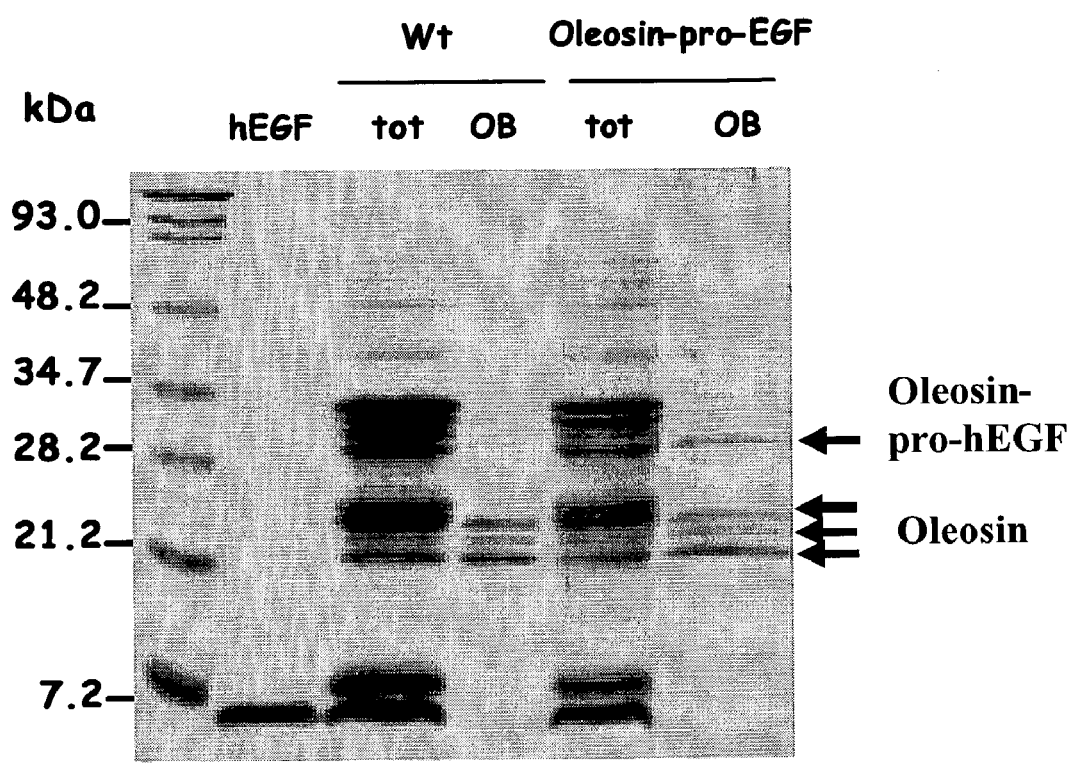
FIG. 3 shows the expression of oleosin-epidermal growth factor fusion protein in transgenic *Arabidopsis* seed and oil body extracts.
Figure 4:
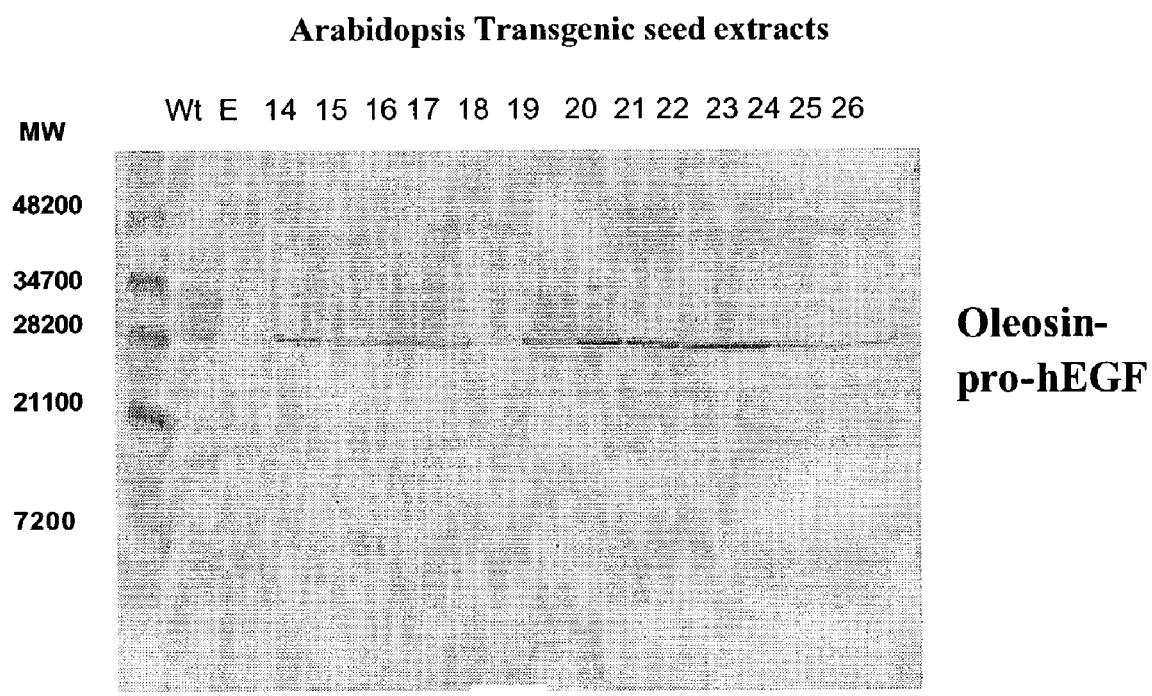
FIG. 4 shows the expression of the oleosin-epidermal growth factor fusion protein in *Arabidopsis* transgenic seed extracts by Western Blot analysis.

The expression of the oleosin-EGF fusion in T2 *Arabidopsis* seeds is shown in FIGS. 3 and 4. FIG. 3 shows the SDS-PAGE comparing seed and oil body extracts in both wild type and transgenic (Oleosin-pro-EGF) *Arabidopsis* seeds. FIG. 4 shows the expression of the oleosin-epidermal growth factor fusion protein in *Arabidopsis* transgenic seed (Oleosin-pro-EGF) extracts by Western Blot analysis. The expression level of the oleosin-epidermal growth factor fusion protein is 0.47% of total seed protein which corresponds to an expression level of 0.12% for the epidermal growth factor portion.

We claim:

1. A method for the expression of an epidermal growth factor in plants said method comprising:

(a) introducing into a plant cell a chimeric nucleic acid sequence comprising:

(1) a first nucleic acid sequence capable of regulating the transcription in said plant cell of (2) a second nucleic acid sequence, wherein said second sequence encodes a recombinant fusion polypeptide and comprises (i) a nucleic acid sequence encoding a sufficient portion of an oil body protein to provide targeting of the recombinant fusion polypeptide to a lipid phase, linked in frame to (ii) a nucleic acid sequence encoding said epidermal growth factor; and (3) a third DNA sequence encoding a termination region functional in said plant cell; and (b) growing said plant cell to produce said recombinant fusion polypeptide.

2. The method according to claim 1 further including separating the recombinant fusion polypeptide from cellular host cell components by selective partitioning into a lipid phase.

3. The method according to claim 1 further including separating the recombinant fusion polypeptide from cellular host components by selective partitioning into a lipid phase comprising oil bodies.

4. A method according to claim 1 wherein said oil body protein is an oleosin, caleosin or steroleosin.

5. A method according to claim 4 wherein said oleosin is SEQ.ID.NO.: 1 or SEQ.ID.NO.: 2, wherein said caleosin is encoded by SEQ.ID.NO.:3 or SEQ.ID.NO.: 4 or wherein said steroleosin is encoded by SEQ.ID.NO.:5.

6. A method according to claim 1 wherein said epidermal growth factor is human or porcine epidermal growth factor.

7. A chimeric nucleic acid sequence encoding a recombinant fusion polypeptide comprising (i) a nucleic acid sequence encoding a sufficient portion of an oil body protein to provide targeting of the recombinant fusion polypeptide to a lipid phase, linked in reading frame to (ii) a nucleic acid sequence encoding an epidermal growth factor.

8. A chimeric nucleic acid sequence according to claim 7 wherein said oil body protein is an oleosin, caleosin or steroleosin.

9. A chimeric nucleic acid sequence according to claim 8 wherein said oleosin is SEQ.ID.NO.: 1 or SEQ.ID.NO.: 2, wherein said caleosin is encoded by SEQ.ID.NO.:3 or SEQ.ID.NO.: 4 or wherein said steroleosin is encoded by SEQ.ID.NO.:5.

10. A chimeric nucleic acid sequence according to claim 7 having the nucleic acid sequence shown in SEQ.ID.NO.: 10.

11. A chimeric nucleic acid sequence according to claim 7 wherein said epidermal growth factor is a human or porcine epidermal growth factor.

12. A chimeric nucleic acid sequence, capable of being expressed in association with an oil body of a plant cell, comprising:

(1) a first nucleic acid sequence capable of regulating the transcription in said plant cell;

(2) a second nucleic acid sequence, wherein said second sequence encodes a recombinant fusion polypeptide and comprises (i) a nucleic acid sequence encoding a sufficient portion of an oil body protein to provide targeting of the recombinant fusion polypeptide to a lipid phase, linked in reading frame to (ii) a nucleic acid sequence encoding an epidermal growth factor; and (3) a third nucleic acid sequence encoding a termination region functional in said plant cell.

13. A chimeric nucleic acid sequence according to claim 12 wherein said oil body protein is an oleosin, caleosin or steroleosin.

14. A chimeric nucleic acid sequence according to claim 13 wherein said oleosin is SEQ.ID.NO.: 1 or SEQ.ID.NO.: 2, wherein said caleosin is encoded by SEQ.ID.NO.:3 or SEQ.ID.NO.: 4 or wherein said steroleosin is encoded by SEQ.ID.NO.:5.

15. A chimeric nucleic acid sequence according to claim 12 wherein said epidermal growth factor is a human or porcine epidermal growth factor.

16. A plant transformed with a chimeric nucleic acid sequence according to claim 12.

17. A plant according to claim 16 wherein said plant is selected from the group consiting of rapeseed (*Brassica* spp.), linseed/flax (*Linum usitatissimum*), safflower (*Carthamus tinctorius*), sunflower (*Helianthus annuus*), maize (*Zea mays*), soybean (*Glycine max*), mustard (*Brassica* spp. and *Sinapis alba*), crambe, (*Crambe abyssinica*), eruca (*Eruca sativa*), oil palm (*Elaeis guineeis*), cottonseed (*Gossypium* spp.), groundnut (*Arachis hypogaea*), coconut (*Cocus nucifera*), castor bean (*Ricinus communis*), coriander (*Coriandrum sativum*), squash, (*Cucurbita maxima*), Brazil nut (*Bertholletia excelsa*) and jojoba (*Simmondsia chinensis*).

18. A plant seed containing a chimeric nucleic acid sequence according to claim 12.

19. A plant seed according to claim 18 wherein said seed is obtained from a dicotelydenous plant.

20. A plant seed according to claim 18 wherein said epidermal growth factor is expressed in the embryogenic tissue of the seed.

21. A plant seed comprising a recombinantly expressed epidermal growth factor, wherein said epidermal growth factor is expressed as a fusion protein with an oil body protein.

22. A plant seed according to claim 21 wherein said epidermal growth to factor is a human or porcine epidermal growth factor.

23. A plant seed according to claim 21 wherein said oil body protein is an oleosin, caleosin or steroleosin.

24. A plant seed according to claim 23 wherein said oleosin is SEQ.ID.NO.: 1 or SEQ.ID.NO.: 2, wherein said caleosin is encoded by SEQ.ID.NO.:3 or SEQ.ID.NO.: 4 or wherein said steroleosin is encoded by SEQ.ID.NO.:5.

25. A plant seed according to claim 21 wherein said epidermal growth factor is expressed in the embryogenic tissue of said seed.

26. A plant seed according to claim 21 wherein said plant seed is obtained from a dicotelydenous plant.

27. A plant seed according to claim 21 wherein said seed is exalbuminous seed.

28. A plant seed according to claim 21 wherein said plant seed is obtained from the group of plants consisting rapeseed (*Brassica* spp.), linseed/flax (*Linum usitatissimum*), safflower (*Carthamus tinctorius*), sunflower (*Helianthus annuus*), maize (*Zea mays*), soybean (*Glycine max*), mustard (*Brassica* spp. and *Sinapis alba*), crambe, (*Crambe abyssinica*), eruca (*Eruca sativa*), oil palm (*Elaeis guineeis*), cottonseed (*Gossypium* spp.), groundnut (*Arachis hypogaea*), coconut (*Cocus nucifera*), castor bean (*Ricinus communis*), coriander (*Coriandrum sativum*), squash, (*Cucurbita maxima*), Brazil nut (*Bertholletia excelsa*) and jojoba (*Simmondsia chinensis*).

* * * * *

SEQUENCE LISTING

<160> NUMBER OF SEQ ID NOS: 11

<210> SEQ ID NO 1
<211> LENGTH: 118
<212> TYPE: PRT
<213> ORGANISM: Arabidopsis thaliana

<400> SEQUENCE: 1

Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
    50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
            100                 105                 110

Phe Ser Trp Ile Tyr Lys
            115

<210> SEQ ID NO 2
<211> LENGTH: 187
<212> TYPE: PRT
<213> ORGANISM: Brassica napus

<400> SEQUENCE: 2

Met Ala Asp Thr Ala Arg Thr His His Asp Val Thr Ser Arg Asp Gln
1               5                   10                  15

Tyr Pro Arg Asp Arg Asp Gln Tyr Ser Met Ile Gly Arg Asp Arg Asp
            20                  25                  30

Gln Tyr Ser Met Met Gly Arg Asp Arg Asp Gln Tyr Asn Met Tyr Gly
        35                  40                  45

Arg Asp Tyr Ser Lys Ser Arg Gln Ile Ala Lys Ala Val Thr Ala Val
    50                  55                  60

Thr Ala Gly Gly Ser Leu Leu Val Leu Ser Ser Leu Thr Leu Val Gly
65                  70                  75                  80

Thr Val Ile Ala Leu Thr Val Ala Thr Pro Leu Leu Val Ile Phe Ser
                85                  90                  95

Pro Ile Leu Val Pro Ala Leu Ile Thr Val Ala Leu Leu Ile Thr Gly
            100                 105                 110

Phe Leu Ser Ser Gly Gly Phe Ala Ile Ala Ala Ile Thr Val Phe Ser
            115                 120                 125

Trp Ile Tyr Lys Tyr Ala Thr Gly Glu His Pro Gln Gly Ser Asp Lys
        130                 135                 140

Leu Asp Ser Ala Arg Met Lys Leu Gly Thr Lys Ala Gln Asp Ile Lys
145                 150                 155                 160

Asp Arg Ala Gln Tyr Tyr Gly Gln Gln His Thr Gly Gly Glu His Asp
                165                 170                 175

Arg Asp Arg Thr Arg Gly Gly Gln His Thr Thr
            180                 185

<210> SEQ ID NO 3
<211> LENGTH: 748
<212> TYPE: DNA
<213> ORGANISM: Arabidopsis thaliana

<400> SEQUENCE: 3

| | | | | | |
|---|---|---|---|---|---|
| taccatgggg | tcaaagacgg | agatgatgga | gagagacgca | atggctacgg | tggctccta | 60 |
| tgcgccggtc | acttaccatc | gccgtgctcg | tgttgacttg | gatgatagac | ttcctaaacc | 120 |
| ttatatgcca | agagcattgc | aagcaccaga | cagagaacac | ccgtacggaa | ctccaggcca | 180 |
| taagaattac | ggacttagtg | ttcttcaaca | gcatgtctcc | ttcttcgata | tcgatgataa | 240 |
| tggcatcatt | tacccttggg | agacctactc | tggactgcga | atgcttggtt | tcaatatcat | 300 |
| tgggtcgctt | ataatagccg | ctgttatcaa | cctgaccctt | agctatgcca | ctcttccggg | 360 |
| gtggttacct | tcacctttct | tccctatata | catacacaac | atacacaagt | caaagcatgg | 420 |
| aagtgattca | aaaacatatg | acaatgaagg | aaggtttatg | ccggtgaatc | ttgagttgat | 480 |
| atttagcaaa | tatgcgaaaa | ccttgccaga | caagttgagt | cttggagaac | tatgggagat | 540 |
| gacagaagga | aaccgtgacg | cttgggacat | ttttggatgg | atcgcaggca | aaatagagtg | 600 |
| gggactgttg | tacttgctag | caagggatga | agaagggttt | ttgtcaaaag | aagctattag | 660 |
| gcggtgtttc | gatggaagct | tgttcgagta | ctgtgccaaa | atctacgctg | gtatcagtga | 720 |
| agacaagaca | gcatactacg | ccatggat | | | | 748 |

<210> SEQ ID NO 4
<211> LENGTH: 738
<212> TYPE: DNA
<213> ORGANISM: Arabidopsis thaliana

<400> SEQUENCE: 4

| | | | | | |
|---|---|---|---|---|---|
| atggggtcaa | agacggagat | gatggagaga | gacgcaatgg | ctacggtggc | tccctatgcg | 60 |
| ccggtcactt | accaccgccg | tgctcgtgtt | gacttggatg | atagacttcc | taaaccttat | 120 |
| atgccaagag | cattgcaagc | accagacaga | gaacacccgt | acggaactcc | aggccataag | 180 |
| aattacggac | ttagtgttct | tcaacagcat | gtctccttct | tcgatatcga | tgataatggc | 240 |
| atcatttacc | cttgggagac | ctactctgga | ctgcgaatgc | ttggtttcaa | tatcattggg | 300 |
| tcgcttataa | tagccgctgt | tatcaacctg | acccttagct | atgccactct | tccggggtgg | 360 |
| ttaccttcac | ctttcttccc | tatatacata | cacaacatac | acaagtcaaa | gcatggaagt | 420 |
| gattcaaaaa | catatgacaa | tgaaggaagg | tttatgccgg | tgaatcttga | gttgatattt | 480 |
| agcaaatatg | cgaaaacctt | gccagacaag | ttgagtcttg | gagaactatg | ggagatgaca | 540 |
| gaaggaaacc | gtgacgcttg | ggacattttt | ggatggatcg | caggcaaaat | agagtgggga | 600 |
| ctgttgtact | tgctagcaag | ggatgaagaa | gggttttttgt | caaaagaagc | tattaggcgg | 660 |
| tgtttcgatg | gaagcttgtt | cgagtactgt | gccaaaatct | acgctggtat | cagtgaagac | 720 |
| aagacagcat | actactaa | | | | | 738 |

<210> SEQ ID NO 5
<211> LENGTH: 1047
<212> TYPE: DNA
<213> ORGANISM: Sesamum indicum

<400> SEQUENCE: 5

| | | | | | |
|---|---|---|---|---|---|
| atggatctaa | tccacacttt | cctcaactta | atagctcccc | ctttcacctt | cttcttcctt | 60 |

-continued

| | |
|---|---|
| ctcttttct tgccacccctt ccagattttc aagttcttcc tttcaatctt gggcacccctt | 120 |
| ttcagcgagg atgtcgctgg aaaagtcgtc gtcatcaccg gcgcctcctc cggcatcggc | 180 |
| gaaagtcttg cttacgagta tgctaagaga gggcgtgct tggtgcttgc tgcaagaagg | 240 |
| gaaaggagtc ttcaagaagt ggccgaaagg gcgcgcgatt tggggtcgcc ggacgtcgtg | 300 |
| gtggtccggg ccgatgtttc gaaggcggag gactgcagga aggttgttga tcagactatg | 360 |
| aatcgctttg gaagattgga tcacctggtc aataacgctg gaattatgtc agtttcaatg | 420 |
| ctggaagaag ttgaagatat tactggttac agagaaacta tggatatcaa cttctggggc | 480 |
| tatgtgtata tgacccgatt tgccgcccca taccttagga atagcagagg ccgaattgtt | 540 |
| gtactttctt catccagttc ttggatgcct actccgagga tgagtttta caatgcaagc | 600 |
| aaagcggcga tttcacaatt ttttgagaca ctgcgggtgg aattcggccc cgatataggc | 660 |
| ataacccttg tgactccagg attcatagaa tctgaactta cccaaggcaa attctacaat | 720 |
| gctggcgaac gtgtaattga tcaggacatg agagatgtac aagtgagcac gactccaatc | 780 |
| ctgagggtgg aaagtgcggc aaggtcaatc gtgaggagcg cgatccgtgg agaaagatac | 840 |
| gtgacagagc cggcctggtt tagggttact tattggtgga agctattctg ccctgaggtg | 900 |
| atggagtggg tatttagact gatgtacttg gccagcccgg gtgagccgga aaggaaacg | 960 |
| tttggcaaga aggttttgga ttacacagga gtgaagtcct tgctttaccc ggaaaccgtg | 1020 |
| caagttccgg agcccaagaa tgattaa | 1047 |

<210> SEQ ID NO 6
<211> LENGTH: 108
<212> TYPE: DNA
<213> ORGANISM: Artificial Sequence
<220> FEATURE:
<223> OTHER INFORMATION: Primer CB 1121

<400> SEQUENCE: 6

| | |
|---|---|
| cagtatggca tctcgagcaa gttcaactct gattcagaat gccctctttc tcatgatgga | 60 |
| tactgtttgc acgatggtgt ttgtatgtat atcgaagctc ttgataag | 108 |

<210> SEQ ID NO 7
<211> LENGTH: 108
<212> TYPE: DNA
<213> ORGANISM: Artificial Sequence
<220> FEATURE:
<223> OTHER INFORMATION: Primer CB 1120

<400> SEQUENCE: 7

| | |
|---|---|
| tttaagcttt tatctaagtt cccaccactt caaatcccta tattggcatc tctcaccatg | 60 |
| tatccaacca cacaattgca tgcgtactta tcaagagctt cgatatac | 108 |

<210> SEQ ID NO 8
<211> LENGTH: 21
<212> TYPE: DNA
<213> ORGANISM: Artificial Sequence
<220> FEATURE:
<223> OTHER INFORMATION: Primer CB 1122

<400> SEQUENCE: 8

| | |
|---|---|
| cagtatggca tctcgagcaa g | 21 |

<210> SEQ ID NO 9
<211> LENGTH: 21
<212> TYPE: DNA
<213> ORGANISM: Artificial Sequence -continued
<220> FEATURE:
<223> OTHER INFORMATION: Primer CB 1123

<400> SEQUENCE: 9
tttaagcttt tatctaagtt c                                              21

<210> SEQ ID NO 10
<211> LENGTH: 1041
<212> TYPE: DNA
<213> ORGANISM: Artificial Sequence
<220> FEATURE:
<223> OTHER INFORMATION: Oleosin-EGF

<400> SEQUENCE: 10
atggcggata cagctagagg aacccatcac gatatcatcg gcagagacca gtacccgatg    60
atgggccgag accgagacca gtaccagatg tccggacgag gatctgacta ctccaagtct   120
aggcagattg ctaaagctgc aactgctgtc acagctggtg gttccctcct tgttctctcc   180
agccttaccc ttgttggaac tgtcatagct ttgactgttg caacacctct gctcgttatc   240
ttcagcccaa tccttgtccc ggctctcatc acagttgcac tcctcatcac cggttttctt   300
tcctctggag ggtttggcat tgccgctata accgttttct cttggattta caagtaagca   360
cacatttatc atcttacttc ataatttgt gcaatatgtg catgcatgtg ttgagccagt   420
agctttggat caatttttttt ggtagaataa caaatgtaac aataagaaat tgcaaattct   480
agggaacatt tggttaacta atacgaaat ttgacctagc tagcttgaat gtgtctgtgt   540
atatcatcta tataggtaaa atgcttggta tgatacctat tgattgtgaa taggtacgca   600
acgggagagc acccacaggg atcagacaag ttggacagtg caaggatgaa gttgggaagc   660
aaagctcagg atctgaaaga cagagctcag tactacggac agcaacatac tggtggggaa   720
catgaccgtg accgtactcg tggtggccag cacactacca tggctgagat cacccgcatt   780
cctctctaca aggtaagtc tctccgtaag gcgctgaagg aacatggact tctagaagac   840
ttcttgcaga acaacagta tggcatctcg agcaagttca actctgattc agaatgccct   900
ctttctcatg atggatactg tttgcacgat ggtgtttgta tgtatatcga agctcttgat   960
aagtacgcat gcaattgtgt ggttggatac attggtgaga gatgccaata tagggatttg  1020
aagtggtggg aacttagata a                                           1041

<210> SEQ ID NO 11
<211> LENGTH: 266
<212> TYPE: PRT
<213> ORGANISM: Artificial Sequence
<220> FEATURE:
<223> OTHER INFORMATION: Oleosin-EGF

<400> SEQUENCE: 11

Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
                20                  25                  30

Arg Gly Ser Asp Tyr Ser Lys Ser Arg Gln Ile Ala Lys Ala Ala Thr
            35                  40                  45

Ala Val Thr Ala Gly Gly Ser Leu Leu Val Leu Ser Ser Leu Thr Leu
        50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile

-continued

```
            85                  90                  95

Thr Gly Phe Leu Ser Ser Gly Gly Phe Gly Ile Ala Ala Ile Thr Val
            100                 105                 110

Phe Ser Trp Ile Tyr Lys Tyr Ala Thr Gly Glu His Pro Gln Gly Ser
        115                 120                 125

Asp Lys Leu Asp Ser Ala Arg Met Lys Leu Gly Ser Lys Ala Gln Asp
    130                 135                 140

Leu Lys Asp Arg Ala Gln Tyr Tyr Gly Gln Gln His Thr Gly Gly Glu
145                 150                 155                 160

His Asp Arg Asp Arg Thr Arg Gly Gly Gln His Thr Thr Met Ala Glu
                165                 170                 175

Ile Thr Arg Ile Pro Leu Tyr Lys Gly Lys Ser Leu Arg Lys Ala Leu
            180                 185                 190

Lys Glu His Gly Leu Leu Glu Asp Phe Leu Gln Lys Gln Gln Tyr Gly
        195                 200                 205

Ile Ser Ser Lys Phe Asn Ser Asp Ser Glu Cys Pro Leu Ser His Asp
    210                 215                 220

Gly Tyr Cys Leu His Asp Gly Val Cys Met Tyr Ile Glu Ala Leu Asp
225                 230                 235                 240

Lys Tyr Ala Cys Asn Cys Val Val Gly Tyr Ile Gly Glu Arg Cys Gln
                245                 250                 255

Tyr Arg Asp Leu Lys Trp Trp Glu Leu Arg
            260                 265
```